United States Patent
Dykstra et al.

(10) Patent No.: US 11,266,637 B2
(45) Date of Patent: Mar. 8, 2022

(54) FORMULATIONS OF TEGAVIVINT AND RELATED COMPOUNDS

(71) Applicant: Iterion Therapeutics, Inc., Houston, TX (US)

(72) Inventors: Steven David Dykstra, Apex, NC (US); Henry Havel, Houston, TX (US); Stephen Horrigan, Houston, TX (US); Roger Harrison, Houston, TX (US); Jeffrey Larson, Houston, TX (US); Jonathan Northrup, Houston, TX (US); Theodore Laslo, Wind Gap, PA (US); Garry Gwozdz, Jim Thorpe, PA (US)

( * ) Notice: Subject to any disclaimer, the term of this patent is extended or adjusted under 35 U.S.C. 154(b) by 96 days.

(21) Appl. No.: 16/428,347

(22) Filed: May 31, 2019

(65) Prior Publication Data

US 2019/0365729 A1 Dec. 5, 2019

Related U.S. Application Data

(60) Provisional application No. 62/679,404, filed on Jun. 1, 2018.

(51) Int. Cl.
| | | |
|---|---|---|
| *A61K 31/444* | (2006.01) | |
| *A61P 11/00* | (2006.01) | |
| *A61K 47/26* | (2006.01) | |
| *A61K 47/34* | (2017.01) | |
| *A61K 31/15* | (2006.01) | |
| *A61K 31/18* | (2006.01) | |
| *A61K 9/12* | (2006.01) | |

(52) U.S. Cl.
CPC ........... *A61K 31/444* (2013.01); *A61K 9/124* (2013.01); *A61K 47/26* (2013.01); *A61K 47/34* (2013.01); *A61P 11/00* (2018.01); *A61K 31/15* (2013.01); *A61K 31/18* (2013.01)

(58) Field of Classification Search
CPC ...... A61K 31/15; A61K 31/18; A61K 31/444; A61K 9/0019; A61K 9/0021; A61K 9/0078; A61K 9/08; A61K 9/10; A61K 9/1075; A61K 9/124; A61K 9/19; A61K 47/10; A61K 47/22; A61K 47/24; A61K 47/26; A61K 47/32; A61K 47/34; A61K 47/44; A61P 11/00
See application file for complete search history.

(56) References Cited

U.S. PATENT DOCUMENTS

| | | | | |
|---|---|---|---|---|
| 2012/0160944 | A1* | 6/2012 | Dodd | A61K 31/192 241/30 |
| 2014/0314672 | A1* | 10/2014 | Trieu | A61K 9/5146 424/9.1 |
| 2017/0029450 | A1* | 2/2017 | Vankayalapati | A61K 45/06 |

FOREIGN PATENT DOCUMENTS

WO WO-2019099836 A1 * 5/2019 ............. A61P 11/00

OTHER PUBLICATIONS

Mandal, "How to Prevent Cancer", News Medical Life Sciences, http://www.news-medical.net/health/How-to-Prevent-Cancer.aspx, pp. 1-4, publ. 2013 (Year: 2013).*
Kaiser, Science, vol. 337, pp. 282-284, publ. 2012 (Year: 2012).*
Williams, "New Understanding of Metastasis Could Lead to Better Treatments", The Scientist, pp. 1-10, publ. 2021 (Year: 2021).*
Pulmonary Fibrosis News, "Pulmonary Fibrosis Prevention", https://pulmonaryfibrosisnews.com/pulmonary-fibrosis-prevention/, pp. 1-5, publ. 2013 (Year: 2013).*
Fett, Clinics in Derm., vol. 31, pp. 432-437, publ. 2013 (Year: 2013).*
Rosenbloom et al., "Human Fibrotic Diseases: Current Challenges in Fibrotic Research", Fibrosis: Methods & Protocols, Chapter 1, pp. 1-23, publ. 2017 (Year: 2017).*

* cited by examiner

*Primary Examiner* — Sarah Pihonak
(74) *Attorney, Agent, or Firm* — Wood, Phillips, Katz, Clark & Mortimer

(57) ABSTRACT

Formulations of tegavivint and related compounds, methods of making such formulations and methods of treating various conditions utilizing such formulations.

11 Claims, 1 Drawing Sheet

Figure 1
Particle Size Distribution
(0.1% Tween 80 Formulation)

Figure 2

Particle Size Distribution
(0.625% Poloxamer Formulation)

FORMULATIONS OF TEGAVIVINT AND RELATED COMPOUNDS

FIELD OF THE INVENTION

The present invention relates generally to formulations of tegavivint and related compounds, methods of making such formulations and methods of treating various conditions utilizing such formulations.

BACKGROUND OF THE INVENTION

Cancer is the second leading cause of death in the United States. It presents complex challenges for the development of new therapies. Cancer is characterized by the abnormal growth of malignant cells that have undergone a series of genetic changes that lead to growth of tumor mass and metastatic properties.

Beta-catenin (β-catenin) is part of a complex of proteins that constitute adherens junctions (AJs). AJs are necessary for the creation and maintenance of epithelial cell layers by regulating cell growth and adhesion between cells. β-catenin also anchors the actin cytoskeleton and may be responsible for transmitting the contact inhibition signal that causes cells to stop dividing once the epithelial sheet is complete.

Wnt/β-catenin pathway has been shown to play a role in cancer. Aberrant β-catenin signaling plays an important role in tumorigenesis. In particular, colorectal cancer is estimated to have greater than 80% mutations in the β-catenin pathway, leading to unregulated oncogenic signaling. Aberrant β-catenin signaling has been shown to be involved in various cancer types, including but not limited to, melanoma, breast, lung, colon, liver, gastric, myeloma, multiple myeloma, chronic myelogenous leukemia, chronic lymphocytic leukemia, T-cell non-Hodgkin lymphomas, colorectal and acute myeloid leukemia (AML) cancers. Further, aberrant Wnt/β-catenin signaling has been found in a large number of other disorders, including osteoporosis, osteoarthritis, polycystic kidney disease, diabetes, schizophrenia, vascular disease, cardiac disease, hyperproliferative disorders, neurodegenerative diseases, and fibrotic diseases including but not limited to idiopathic pulmonary fibrosis (IPF), Dupuytren's contracture, Nonalcoholic steatohepatitis (NASH), and others. Myeloproliferative neoplasms (MPNs) are a closely related group of hematological malignancies in which the bone marrow cells that produce the body's blood cells develop and function abnormally. The three main myeloproliferative neoplasms are Polycythemia Vera (PV), Essential Thrombocythemia (ET) and Primary Myelofibrosis (PMF). A gene mutation in JAK2 is present in most PV patients and 50% of ET and PMF patients. The beta catenin pathway is activated in MPN in many cases and required for survival of these cells.

Tegavivint and related compounds are described, for example, in U.S. Pat. No. 8,129,519. Tegavivint has the following structural formula:

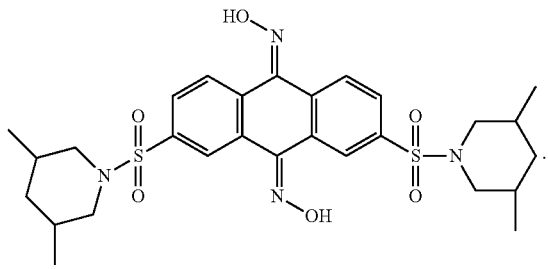

The molecular formula of tegavivint is $C_{28}H_{36}N_4O_6S_2$.
The molecular mass of tegavivint is 588.20763 amu.

There is a need in the art to provide stable, readily bioavailable formulations of tegavivint and related compounds, wherein the formulations allow administration via different routes of administration, including but not limited to, parenteral and via inhalation, and are stable to be suitable for a clinical study and treatment of various diseases which are treatable with tegavivint.

SUMMARY OF THE INVENTION

It has been very challenging and difficult to develop a stable, non-toxic formulation of tegavivint. A large number of formulations were developed and tested; however, they had poor bioavailability and/or proved unstable upon storage, and/or turned to be highly toxic. These formulations include microemulsions, solid suspensions, liposome-based formulations, various oral formulations, and IV formulations.

The inventors have unexpectedly and surprisingly discovered that a nanosuspension of tegavivint works, wherein the nanosuspension comprises a surfactant and wherein the particles of tegavivint have an effective D50 of less than or equal to 500 nm and D90 of less than or equal to 1.0 micrometer (μm) when measured using laser diffraction. It has also been discovered that a particularly preferred concentration of tegavivint is 10-25 mg/ml, most preferably 25 mg/ml; a preferred surfactant is a poloxamer surfactant (preferably, Poloxamer 188), preferably at a concentration of 0.625%; and that the nanosuspension should preferably include a polyol, and more preferably sorbitol.

The most preferred formulation, therefore, is a composition that comprises tegavivint at 25 mg/ml; Poloxamer 188 at 0.625% and 10% sorbitol, wherein tegavivint is in the form of a nanosuspension comprising particles of tegavivint, and wherein the particles have an effective D50 of less than or equal to 500 nm and D90 of less than or equal to 1.0 micrometer (μm) when measured using laser diffraction.

Thus, in one embodiment, the invention provides a composition comprising:
a) particles of a compound of formula I

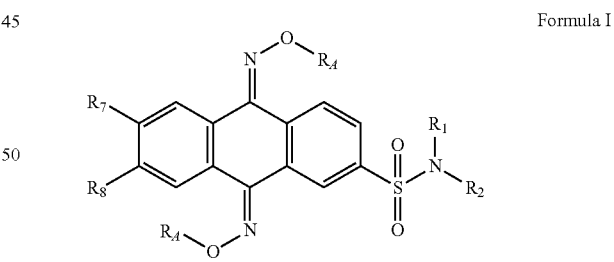

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring, or a pharmaceutically acceptable salt, ester, amide, stereoisomer or geometric isomer thereof; and
b) a surfactant;
wherein the particles have an effective D50 of less than or equal to 500 nm and D90 of less than or equal to 1.0 micrometer (μm) when measured using laser diffraction.

In some embodiments, the effective average particle size of the compounds is about 4900 nm, about 4800 nm, about 4700 nm, about 4600 nm, about 4500 nm, about 4400 nm, about 4300 mm, about 4200 nm, about 4100 nm, about 4 microns, about 3900 nm, about 3800 nm, about 3700 nm, about 3600 nm, about 3500 nm, about 3400 mm, about 3300 nm, about 3200 nm, about 3100 nm, about 3 microns, about 2900 mm, about 2800 nm, about 2700 nm, about 2600 nm, about 2500 nm, about 2400 nm, about 2300 nm, about 2200 nm, about 2100 nm, about 2000 nm, about 1900 nm, about 1800 nm, about 1700 nm, about 1600 nm, about 1500 nm, about 1400 nm, about 1300 nm, about 1200 nm, about 1100 nm, about 1000 nm, about 900 nm, about 800 nm, about 700 nm, about 600 nm, about 500 nm, about 400 nm, or about 300 nm.

Further, in some embodiments, the effective average particle size of the compounds is less than 900 nm, more preferably less than 500 nm, and even more preferably, less than 300 nm.

In a preferred embodiment, the surfactant is a poloxamer surfactant.

In another preferred embodiment, the poloxamer surfactant is Poloxamer 188.

In a preferred embodiment, the particulate composition further comprises a stabilizer.

In a preferred embodiment, the stabilizer is selected from the group consisting of a sugar, a polyol, a polysorbate surfactant and polyvinylpyrrolidone (PVP).

In another preferred embodiment, the sugar is selected from the group consisting of sucrose and/or trehalose.

In a preferred embodiment, the polyol comprises sorbitol and/or mannitol.

In one embodiment, the concentration of the compound in the provided compositions is between about 1 mg/ml and about 100 mg/ml, more preferably between about 10 mg/ml and about 50 mg/ml, more preferably between about 10 mg/ml and about 25 mg/ml and even more preferably about 25 mg/ml.

In one embodiment, the compositions of the invention are prepared by milling.

In another embodiment, the compositions of the invention are prepared by LyoCell technology. U.S. Pat. No. 7,713,440 describes the LyoCell technology. The contents of U.S. Pat. No. 7,713,440 are hereby incorporated by reference in its entirety.

In another embodiment, the compositions of the invention can be prepared by a dry milling approach such as that described in U.S. Pat. No. 8,808,751. The contents of U.S. Pat. No. 8,808,751 are hereby incorporated by reference in its entirety. By proper selection of milling media and suitable grinding compounds, it is possible to generate a nanoparticulate composition from conventional drug substance particles and to prevent agglomeration of the small particles created in the dry milling apparatus.

In yet another embodiment, the compositions of the invention can be prepared by a process utilizing human serum albumin as a carrier, such as a process described in U.S. Pat. No. 6,537,579. The contents of U.S. Pat. No. 6,537,579 are hereby incorporated by reference in its entirety. This process may be particularly suited for making nanoparticulate compositions of poorly water-soluble compounds. Compositions created by such a process may allow for effective administration of biologically active compounds that are poorly water-soluble.

In another embodiment, nanoparticulate compositions containing polymers such as poly(DL-lactide-co-glycolide) are able to deliver poorly soluble biologically active compounds. As shown in U.S. Pat. No. 5,543,158, these compositions can be designed to be long-acting vehicles. The contents of U.S. Pat. No. 5,543,158 are hereby incorporated by reference in its entirety.

In another embodiment, compositions of the invention can be prepared as polymeric micelles which have been successful in improving the solubility of biologically active compounds. A marketed product using this technology, Genexol-PM, incorporates the anti-cancer drug paclitaxel and was approved in South Korea in 2007.

In one embodiment, the invention provides a process of preparing a composition comprising the following steps (a) through (c):

a) mixing particles of the compound of formula I

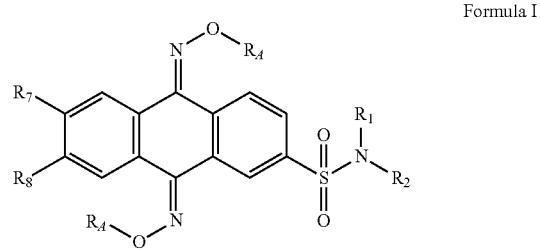

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring, or a pharmaceutically acceptable salt, ester, amide, stereoisomer or geometric isomer thereof;

with a surfactant and an acceptable carrier to produce a suspension;

b) using a roller mill or high energy mill to mill the suspension of step (a); and c) adding a polyol to the particles of step (b).

In one embodiment, the acceptable carrier is a liquid carrier (e.g., water).

In one embodiment, the suspension is an aqueous suspension.

In another embodiment, the process of preparing a composition comprises the following steps (a) through (b):

a) mixing particles of the compound of formula I

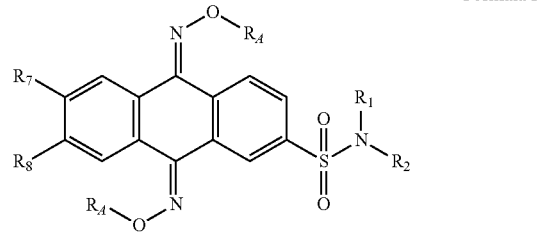

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring, or a pharmaceutically acceptable salt, ester, amide, stereoisomer or geometric isomer thereof;

with a surfactant, a polyol and an acceptable carrier to produce a suspension; and b) using a roller mill or high energy mill to mill the suspension of step (a).

In one embodiment, the acceptable carrier is a liquid carrier (e.g., water).

In one embodiment, the suspension is an aqueous suspension.

In a preferred embodiment, the compositions of the invention exhibit long term stability.

In a preferred embodiment, the compositions of the invention are nanoparticulate compositions.

In a preferred embodiment, the compound of formula I in the compositions of the invention has the following structure:

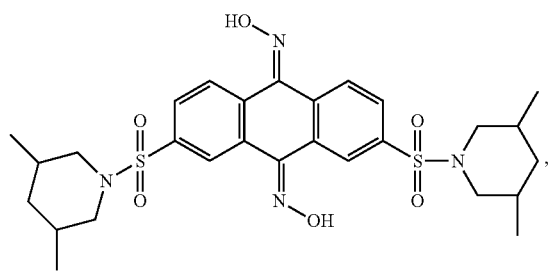

or a pharmaceutically acceptable salt, ester, amide, stereoisomer or geometric isomer thereof.

The compound having the formula above is also known as tegavivint (BC2059).

In one embodiment, the compositions of the invention may be formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration, including intramuscular, subcutaneous, intravenous and intradermal injection; (d) any combination of (a), (b) and (c).

The compositions of the invention can further comprise one or more pharmaceutically acceptable excipients, carriers, or a combination thereof.

In another embodiment, the invention provides a method of preventing, treating or ameliorating cancer or tumor metastasis in a mammal in need thereof comprising administering to said mammal an effective amount of the compositions of the invention.

The method of administering is not limited to any specific route of administration, and includes, but is not limited to, intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods.

In another embodiment, the method of preventing, treating or ameliorating cancer or tumor metastasis in a mammal in need thereof can include administering an additional anti-cancer agent and/or cancer therapy (for example, cancer vaccines, anti-cancer adoptive cell therapies and radio therapies).

In one embodiment, the additional anti-cancer agent is selected from the group consisting of antimitotic agents, antimetabolite agents, HDAC inhibitors, proteosome inhibitors, immunotherapeutic agents, FLT-3 EGFR, MEK, PI3K and other protein kinase inhibitors, LSD1 inhibitors, and WNT pathway inhibitors, alkylating agents and DNA repair pathway inhibitors, anti-hormonal agents, anti-cancer antibodies, and other cytotoxic chemotherapy agents.

In another embodiment, the invention provides a method of treating and/or preventing a fibrotic disease in a mammal in need thereof comprising administering to said mammal an effective amount of the compositions of the invention.

In a preferred embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, and reactive fibrosis.

In one embodiment, the method of treating and/or preventing a fibrotic disease in a mammal in need thereof can include administering an additional anti-fibrotic agent.

BRIEF DESCRIPTION OF THE DRAWINGS

FIG. 1 is a graph of Particle Size Distribution (PSD) of one of the inventive formulations.

FIG. 2 is a graph of PSD of another one of the inventive formulations.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "tegavivint" refers to a compound having the following structure:

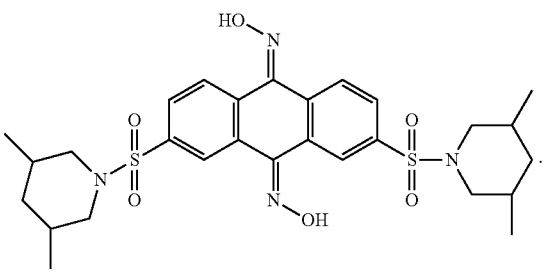

The term "BC2059" is used interchangeably with "tegavivint."

The term "long-term storage" or "long-term stability" is understood to mean that the pharmaceutical composition can be stored for three months or more, for six months or more, and preferably for one year or more. Long term storage is also understood to mean that the pharmaceutical composition is stored at 2-8° C. or at room temperature 15-25° C.

The term "stable" or "stabilized" with respect to long-term storage is understood to mean that active ingredient contained in the pharmaceutical compositions does not lose more than 20%, or more preferably 15%, or even more preferably 10%, and most preferably 5% of its activity relative to activity of the composition at the beginning of storage.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "treatment" refers to any administration or application of remedies for disease in a mammal and includes inhibiting the disease, arresting its development, relieving the disease (for example, by causing regression, or restoring or repairing a lost, missing, or defective function) or stimulating an inefficient process. The term includes obtaining a desired pharmacologic and/or physiological effect and covering any treatment of a pathological condition or disorder in a mammal. The effect may be prophylactic in terms of completely or partially preventing a disorder or symptom thereof and/or may be therapeutic in terms of a partial or complete cure for a disorder and/or adverse effect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "therapeutically effective amount" refers to an amount which, when administered to a living subject, achieves a desired effect on the living subject. For example, an effective amount of the compositions of the invention for administration to the living subject is an amount that prevents and/or treats any of the diseases mediated via the Wnt/β-catenin pathway. The exact amount will depend on the purpose of the treatment and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "composition" or "formulation" refers to a mixture that usually contains a carrier, such as a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses or powders. The terms "composition," "pharmaceutical composition" and "formulation" are used interchangeably.

The term "nanoparticulate composition" refers to compositions wherein all, or almost all of the particles are less than 1000 nM.

Compositions of the Invention

In one embodiment, the invention provides a composition comprising:
a) particles of a compound of formula I

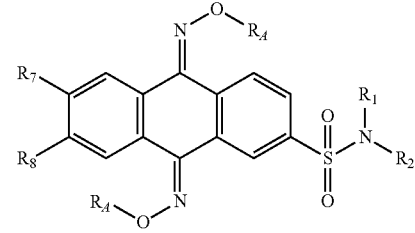

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring,
or a pharmaceutically acceptable salt, ester, amide, stereoisomer or geometric isomer thereof; and
b) a surfactant;
wherein the particles have an effective D50 of less than or equal to 500 nm and D90 of less than or equal to 1.0 micrometer (μm) when measured using laser diffraction.

D50 is also known as median diameter of particle size distribution. It refers to the value of the particle diameter at 50% in the cumulative distribution. In other words, when D50 value is less than or equal to 500 nm, it means that 50% of the particles are less than 500 nm in diameter.

D90 refers to the percentage of the particles under the reported particle size. In other words, when D90 value is less than or equal to 1.0 μm, it means that 90% of the particles are less than 1.0 μm in diameter.

In some embodiments, the effective average particle size of the compounds is about 4900 nm, about 4800 nm, about 4700 nm, about 4600 nm, about 4500 nm, about 4400 nm, about 4300 mm, about 4200 nm, about 4100 nm, about 4 microns, about 3900 nm, about 3800 nm, about 3700 nm, about 3600 nm, about 3500 nm, about 3400 mm, about 3300 nm, about 3200 nm, about 3100 nm, about 3 microns, about 2900 mm, about 2800 nm, about 2700 nm, about 2600 nm, about 2500 nm, about 2400 nm, about 2300 nm, about 2200 nm, about 2100 nm, about 2000 nm, about 1900 nm, about 1800 nm, about 1700 nm, about 1600 nm, about 1500 nm, about 1400 nm, about 1300 nm, about 1200 nm, about 1100 nm, about 1000 nm, about 900 nm, about 800 nm, about 700 nm, about 600 nm, about 500 nm, about 400 nm, or about 300 nm.

Further, in some embodiments, the effective average particle size of the compounds is less than 900 nm, more preferably less than 500 nm, and even more preferably, less than 300 nm.

In a preferred embodiment, the surfactant is a poloxamer surfactant.

In another preferred embodiment, the poloxamer surfactant is Poloxamer 188.

In a preferred embodiment, the composition further comprises a stabilizer.

In a preferred embodiment, the stabilizer is selected from the group consisting of a sugar, a polyol, a polysorbate surfactant and polyvinylpyrrolidone (PVP).

In another preferred embodiment, the sugar is selected from the group consisting of sucrose and/or trehalose.

In a preferred embodiment, the polyol comprises sorbitol and mannitol.

In one embodiment, the concentration of the compound in the provided compositions is between about 1 mg/ml and about 100 mg/ml, more preferably between about 10 mg/ml and about 50 mg/ml, more preferably between about 10 mg/ml and about 25 mg/ml and even more preferably about 25 mg/ml.

A particularly preferred concentration of tegavivint is 10-25 mg/ml, most preferably 25 mg/ml; a preferred surfactant is a poloxamer surfactant (preferably, Poloxamer 188), preferably at a concentration of 0.625%; and the nanosuspension preferably includes a polyol, and more preferably sorbitol.

The most preferred formulation, therefore, is a nanosuspension that comprises tegavivint at 25 mg/ml; Poloxamer 188 at 0.625% and 10% sorbitol.

In one embodiment, the compositions of the invention are prepared by milling, preferably wet milling.

In one embodiment, the invention provides a process of preparing a composition comprising the following steps (a) through (c):

a) mixing particles of the compound of formula I

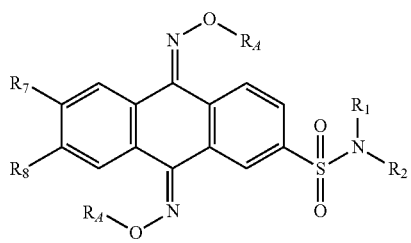

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring, or a pharmaceutically acceptable salt, ester, amide, stereoisomer or geometric isomer thereof;

with a surfactant and an acceptable carrier to produce a suspension;

b) using a roller mill or high energy mill to mill the suspension of step (a); and c) adding a polyol to the particles of step (b).

In one embodiment, the acceptable carrier is a liquid carrier (e.g., water).

In one embodiment, the suspension is an aqueous suspension.

In another embodiment, the process of preparing a composition comprises the following steps (a) through (b):

a) mixing particles of the compound of formula I

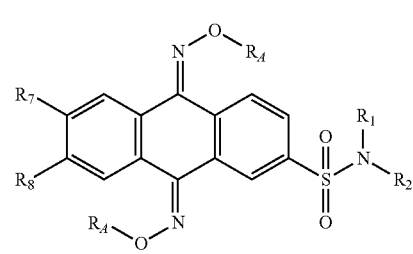

Formula I wherein $R_4$ is hydrogen, $R_7$ and $R_8$ are independently selected from H and $SO_2NR_3R_4$, wherein one of $R_7$ and $R_8$ is hydrogen and wherein $NR_1R_2$ and $NR_3R_4$ are independently 6- to 15-membered heterocycloalkyl containing one nitrogen in the ring, or a pharmaceutically acceptable salt, ester, amide, stereoisomer or geometric isomer thereof;

with a surfactant, a polyol and an acceptable carrier to produce a suspension; and b) using a roller mill or high energy mill to mill the suspension of step (a).

In one embodiment, the acceptable carrier is a liquid carrier (e.g., water).

In one embodiment, the suspension is an aqueous suspension.

In another embodiment, the compositions of the invention are prepared by LyoCell technology. U.S. Pat. No. 7,713,440 describes the LyoCell technology. The contents of U.S. Pat. No. 7,713,440 are hereby incorporated by reference in its entirety.

In another embodiment, the compositions of the invention can be prepared by a dry milling approach such as that described in U.S. Pat. No. 8,808,751. The contents of U.S. Pat. No. 8,808,751 are hereby incorporated by reference in its entirety. By proper selection of milling media and suitable grinding compounds, it is possible to generate a nanoparticulate composition from conventional drug substance particles and to prevent agglomeration of the small particles created in the dry milling apparatus.

In yet another embodiment, the compositions of the invention can be prepared by a process utilizing human serum albumin as a carrier, such as a process described in U.S. Pat. No. 6,537,579. The contents of U.S. Pat. No. 6,537,579 are hereby incorporated by reference in its entirety. This process may be particularly suited for making nanoparticulate compositions of poorly water-soluble compounds. Compositions created by such a process may allow for effective administration of biologically active compounds that are poorly water-soluble.

In another embodiment, nanoparticulate compositions containing polymers such as poly(DL-lactide-co-glycolide) are able to deliver poorly soluble biologically active compounds. As shown in U.S. Pat. No. 5,543,158, these compositions can be designed to be long-acting vehicles. The contents of U.S. Pat. No. 5,543,158 are hereby incorporated by reference in its entirety.

In another embodiment, compositions of the invention can be prepared as polymeric micelles which have been successful in improving the solubility of biologically active compounds. A marketed product using this technology, Genexol-PM, incorporates the anti-cancer drug paclitaxel and was approved in South Korea in 2007.

In a preferred embodiment, the compositions of the invention exhibit long term stability.

In one embodiment, the compositions of the invention are nanoparticulate compositions.

In a preferred embodiment, the compound of formula I in the compositions of the invention has the following structure:

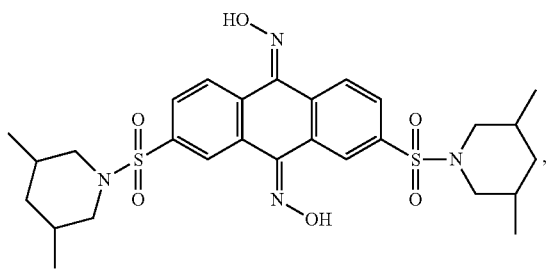

or a pharmaceutically acceptable salt, ester, amide, stereoisomer or geometric isomer thereof.

This compound is also known as tegavivint.

The invention encompasses formulations including tegavivint and a pharmaceutically acceptable salt, ester, amide, stereoisomer or geometric isomer thereof.

Tegavivint solubility in water has been measured across the pH range of 2 to 10 and was found to be <0.25 mcg/mL across the range.

In organic solvents, tegavivint has solubilities as shown: DMSO (334 µg/mL), ethanol (260 µg/mL), methanol (299 µg/mL), acetone (1 mcg/mL), dichloromethane:ethanol (1:4) (1 mg/mL).

In one embodiment, the compositions of the invention may be formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration, including intramuscular, subcutaneous, intravenous and intradermal injection; (d) any combination of (a), (b) and (c).

The compositions of the invention can further comprise one or more pharmaceutically acceptable excipients, carriers, or a combination thereof.

The pharmaceutically acceptable excipients used in the formulation of the present invention can act in more than one way. The role of dispersant, for example, is principally to allow individual particles to remain separated, i.e. to minimize agglomeration. However, this ingredient might also impart changes to surface tension of the formulation, for instance, and might act to reduce viscosity.

The pharmaceutically acceptable excipients can be, for example, a dispersion medium, a dispersion emulsifier, a dispersion enhancer, or a combination thereof.

Examples of the propellant include, but not limited to, HFA-134a (1, 1, 1, 2-tetrafluoroethane), HFA-227 (1,1,1,2,3,3,3-heptafluoropropane), a combination thereof, etc.

The dispersion medium can be, for example, ethanol, propylene glycol, polyethylene glycol 200, polyethylene glycol 300, polyethylene glycol 400, glycerin, a combination thereof, etc.

The dispersion emulsifier (enhancer) can be, for example, $H_2O$, oleic acid, sodium lauryl sulfate, polyethylene glycol 1000, ammonium alginate, potassium alginate, calcium stearate, glyceryl monooleate, polyoxyethylene stearates, emulsifying wax, polysorbate 20, polysorbate 40, polysorbate 60, polysorbate 80, sorbitan monolaurate, sorbitan monooleate, sorbitan monopalmitate, sorbitan monostearate, sorbitan sesquioleate, sorbitan trioleate, poloxamer, a combination thereof, etc.

Examples of the dispersion enhancers include, but not limited to, polysorbate 20, polysorbate 40, polysorbate 60, polysorbate 80, carboxymethylcellulose sodium, hypromellose, ethylene glycol stearates, sorbitan monolaurate, sorbitan monooleate, sorbitan monopalmitate, sorbitan monostearate, sorbitan sesquioleate, sorbitan trioleate, glyceryl monostearate, lecithin, meglumine, poloxamer, polyoxyethylene alkyl ethers, polyoxyl 35 castor oil, polyoxyethylene stearates, polyoxylglycerides, pyrrolidone, sorbitan esters, stearic acid, vitamin E polyethylene glycol succinate, polyethylene glycol 1000, povidone, a combination thereof, etc.

The compositions of the invention can be suitable for all routes of administration, including but not limited to, intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In a preferred embodiment, the compound of formula I has the following structure:

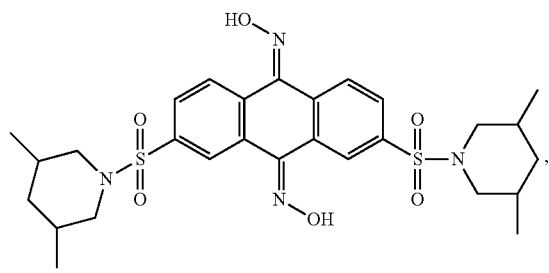

or a pharmaceutically acceptable salt, ester, amide, stereoisomer or geometric isomer thereof.

In another embodiment, the invention provides a method of preventing, treating or ameliorating cancer or tumor metastasis in a mammal in need thereof comprising administering to said mammal an effective amount of the compositions of the invention.

In another embodiment, the method of preventing, treating or ameliorating cancer or tumor metastasis in a mammal in need thereof can include administering an additional anti-cancer agent and/or cancer therapy (for example, cancer vaccines, anti-cancer adoptive cell therapies and radio therapies).

In one embodiment, the additional anti-cancer agent is selected from the group consisting of antimitotic agents, antimetabolite agents, HDAC inhibitors, proteosome inhibitors, immunotherapeutic agents, FLT-3 EGFR, MEK, PI3K and other protein kinase inhibitors, LSD1 inhibitors, and WNT pathway inhibitors, alkylating agents and DNA repair pathway inhibitors, anti-hormonal agents, anti-cancer antibodies, and other cytotoxic chemotherapy agents.

In another embodiment, the invention provides a method of treating and/or preventing a fibrotic disease in a mammal in need thereof comprising administering to said mammal an effective amount of the nanoparticulate compositions of the invention.

In a preferred embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis.

The present invention is more particularly described in the following examples that are intended as illustrative only, since many modifications and variations therein will be apparent to those skilled in the art. In the following examples it should be understood that weight percentages of various ingredients are expressed as w/v percentages.

EXAMPLES OF THE INVENTION

It was very challenging and difficult to arrive at a formulation of tegavivint that worked: i.e., was stable and not toxic.

The formulation that worked turned out to be a nanosuspension of tegavivint, wherein the nanosuspension comprises a surfactant and wherein the particles of tegavivint have an effective D50 of less than or equal to 500 nm and D90 of less than or equal to 1.0 micrometer (μm) when measured using laser diffraction. It has also been discovered that a particularly preferred concentration of tegavivint is 10-25 mg/ml, most preferably 25 mg/ml; a preferred surfactant is a poloxamer surfactant (preferably, Poloxamer 188), preferably at a concentration of 0.625%; and that the nanosuspension should preferably include a polyol, and more preferably sorbitol.

The Examples section first describes multiple experiments to formulate tegavivint that ultimately failed for various reasons. Then, the section describes a milling feasibility experiment which demonstrated that tegavivint could be roller milled when suspended in aqueous solutions with various dispersants. However, even when roller milled, multiple formulations of tegavivint were still unsuccessful.

Finally, it describes successful experiments which involved the claimed nanosuspension of tegavivint.

Unsuccessful Experiments

Example 1

A Microemulsion Formulation of Tegavivint was Very Toxic

A microemulsion formulation of tegavivint was developed, wherein the formulation contained 20 mg/ml BC2059, 10% Tween (polysorbate 80), 30% ethanol, 50% propylene glycol (PG) and 10% D-α-tocopherol polyethylene glycol 1000 succinate.

Although good stability of the formulation was observed, the formulation was extremely toxic to rodents and therefore not pursued further.

Example 2

Liposome-Based Formulations were Unstable

Based on preliminary studies, two liposome formulations of BC2059 were chosen as the leads for scale-up at 100 ml and stability evaluation.

The first was 100% ePC formulation with 15:1 lipid to drug ratio.

The other lead formulation included 80:20% ePC: LysoPC lyposomes at 10:1 lipid to drug ratio.

Both of these formulations proved to be unstable upon storage at 5° C. (precipitation was observed). Furthermore, the formulations were also unstable upon freezing.

Example 3

Oral and IV Formulations were Unsuccessful

An oral formulation of tegavivint containing soy lecithin, PEG200, PEG400, PG, and TPGS was initially elected as the lead oral formulation. However, this lead oral formulation showed poor bioavailability in the dog study and therefore was not pursued.

Upon further screening, an IV based formulation was elected as the next lead. This IV formulation comprised an oil phase (vegetable oil and Polysorbate 80 (PS80) as solubilizers) and soy lecithin as the emulsifier. The formulation had the following ingredients (all numbers are weight %):

BC2059: 1%; PS80: 10%; Miglyol 812: 12%; soy lecithin (LIPOID S-100): 12%; propylene glycol (PG): 50%; deionized water: to qs.

This formulation showed potential for filtration through 0.2 micron with minimal loss along with good physical and chemical stability. However, due to high toxicity in the rodent study, this formulation was not pursued further.

Experiments Involving Nanosuspensions of Tegavivint

Example 4

Milling Feasibility

First, it was determined whether milling is feasible in principle. The experiment demonstrated that it is.

Milling feasibility was initiated by roller milling laboratory-scale batches of tegavivint suspended at 5% (50 mg/mL) in aqueous solutions the following dispersants, selected for their suitability for intravenous administration:

Polysorbate 20 (0.5%)

Poloxamer 188 (0.5%)

Polyvinylpyrrolidone, K17 (1%)

Polyvinylpyrrolidone, K17 (1%) and sodium deoxycholate (0.25%)

Lecithin (1%)

5-mL test suspensions were milled each with a media charge of approximately 10 mL of 0.5-mm diameter yttria-stabilized zirconia (YTZ) milling media and were sampled periodically for particle-size distribution analysis by laser diffraction. After twelve hours of milling, only the poloxamer and the polyvinylpyrrolidone suspensions showed the production of a uniform nanoparticulate dispersion, with the lecithin suspension showing no appreciable size reduction, the polysorbate suspension exhibiting caking of the BC2059 inside of the milling container, and the polyvinylpyrrolidone/sodium deoxycholate suspension showing high aspect-ratio crystals. Finished test suspensions were allowed to stand at uncontrolled ambient conditions for four days for informal particle-size stability. All tested suspensions showed some degree of particulate growth, with particle elongation similar to what had been seen initially in the polyvinylpyrrolidone/sodium deoxycholate suspension.

To try to prevent crystal growth, preparations were made at 5% (50 mg/mL) tegavivint using both poloxamer and polyvinylpyrrolidone (PVP) as dispersants and incorporating sucrose, sorbitol, and trehalose, each at 10%. Milling and storage were done under similar conditions to the initial feasibility experiment. All preparations milled down to a nanosuspension, but none of the additives appeared to have a discernable effect on crystal growth inhibition. For further work, poloxamer 188 was chosen as the primary dispersant.

Additional material was milled at 5% (50 mg/mL) in poloxamer 188. To facilitate an increase in scale, the poloxamer content was increased from 1% to 1.5% to ensure a uniform nanosuspension. Milled nanosuspension was diluted to produce a 2% (20 mg/mL) BC2059/0.6% poloxamer/0.9% sodium chloride formulation for use in initial pharmacokinetic work to be done by a third party. The remaining milled concentrated material was reserved to test the effectiveness of lyophilization on preventing the apparent crystal growth.

This formulation was then tested in the experiment described in Example 5.

Example 5

Lyophilization Feasibility

This experiment was supposed to determine if lyophilization is feasible in principle. It showed that in principle, tegavivint can be lyophilized.

The 5% (50 mg/mL) tegavivint poloxamer aqueous suspension was diluted with various potential cryoprotectant-containing diluents so that the final concentrations were 2% (20 mg/mL) tegavivint, 0.6% poloxamer, and the following:

Sucrose (10%)
Mannitol (5%)
Sucrose (5%) and mannitol (2.5%)
Sorbitol (10%)
Sorbitol (5%) and mannitol (2.5%)
Trehalose (10%)
Trehalose (5%) and mannitol (2.5%)

5-mL serum vials were filled to 2 mL with each preparation and lyophilized at −40° C. and 100 mTorr pressure. The dried vials were resuspended with purified water and analyzed for particle-size distribution. Of the systems tested, only the 10% sorbitol and the 10% trehalose resuspensions returned particle-size distributions that were comparable to the pre-lyophilized suspension. Additional nanosuspension was milled, increasing the component concentrations to 10% (100 mg/mL) BC2059 and 3% poloxamer to increase milling efficiency and to facilitate larger batch manufacture.

The following suspensions were prepared from the milled material for low-temperature differential scanning calorimetry (DSC) analysis:

2% (20 mg/mL) BC2059 with 0.6% polysorbate and 10% sorbitol

2% (20 mg/mL) BC2059 with 0.6% polysorbate and 10% trehalose.

DSC analysis, performed from 25° C. to −40° C. and then back to 25° C. at a rate of 1° C. per minute, gave the following glass transition values for the suspensions:

Sorbitol suspension: −18° C.
Trehalose suspension: −33° C.

The suspensions were lyophilized, with 2 mL fill in 5-mL vials, with primary drying at −30° C./150 mTorr and with secondary drying at −16° C./550 mTorr. Informally, lyophilized samples were shown to be physically stable, with reproducible uniform size distributions, for up to one week at ambient lab conditions. For subsequent work, sorbitol was chosen over trehalose because of both the higher glass-transition temperature and the greater availability of historical toxicity data on the former.

A test batch was milled and lyophilized with primary drying at −24° C./250 mTorr and secondary drying at −16° C./500 mTorr to provide materials for an animal study. The milling was done at 20% (200 mg/mL) tegavivint with a poloxamer content of 5% to try to facilitate larger batch sizes and to enhance milling efficiency. The dried formulation measured at about 1% water by Karl Fischer and showed adequate particle-size stability after 24 hours when reconstituted with purified water.

These formulations were then tested in the experiment described in Example 6.

Example 6

Nonclinical Toxicology/Pharmacokinetics Batch Production

The purpose of this experiment was to test the lyophilized formulations of tegavivint.

Four sequentially prepared sub-batches of suspension, each representing 15 g of tegavivint, were milled at the increased loading and were extracted from the milling media using a diluent of 11.43% sorbitol aqueous solution to enhance the product yield and to result in a suspension of 2% (20 mg/mL) tegavivint/0.5% poloxamer/10% sorbitol.

Sub-batches were filled at 2 mL into 5-mL vials and lyophilized at the previously optimized conditions. Although some of the vials showed signs of meltback, likely due to the increase in batch scale, the dried material resuspended readily into uniform nanosuspensions. The interim assay, PSD, and water results for each sub-batch of vials showed acceptable batch-to-batch agreement, so the four sets of vials were combined and treated as a single batch for stability and animal study use. See Table 1 below.

TABLE 1

| Sub-Batch | Assay (% LC) | D90 (um) | Water (% w/w) |
|---|---|---|---|
| 1 | 97.3 | 0.19 | 1.9 |
| 2 | 103.1 | 0.18 | 1.5 |
| 3 | 111.3 | 0.18 | 1.1 |
| 4 | 105.9 | 0.19 | 1.1 |

During milling, one of the sub-batches failed because of stable foam production, which prevented further milling and resulted in permanent particle aggregation. It was discarded and another batch was made to replace it. In the production of the failing batch, a 250-mL serum bottle was used instead of a media bottle to facilitate PSD sampling during milling. The foaming was attributed to the difference in dimensions of the bottle which ostensibly allowed the entrainment of air, resulting in the batch failure. During the extraction of all batches, dark insoluble particulate was isolated from the milling media. This material was later analyzed by XRPD and found to be fused aggregates of tegavivint.

At the one-month stability point, the composited batch exhibited significant particle-size increase, attributed to aggregation of poloxamer rather than ripening or crystal growth of the API (drug substance). Attempts were made to determine a lab-suitable path by which the test articles could be salvaged for use. Samples were reconstituted, resealed, and heated to 50° C. for up to 3 hours without reducing the aggregates. Autoclaving the resuspended vials at 121° C. for 10 minutes using a slow-release liquid cycle and allowing them to cool to ambient conditions returned an acceptable particle-size distribution.

As this kind of treatment did not present a suitable path forward, the decision was made to re-formulate the product.

Example 7

Re-Formulating Compositions and Lyophilization Ultimately Failed but Liquid Suspension Containing Poloxamer Appeared Promising In this experiment, additional re-formulated compositions of tegavivint were tested. Ultimately, lyophilization did not work but liquid suspension (nanosuspension) showed promising results.

Feasibility-scale batches were made in some of the originally tested dispersants, but using the increased 20% (200 mg/mL) tegavivint concentration, as this change might have made feasible a dispersant that had not shown promise at 5% (5 mg/mL). The following dispersants were tested alongside a 5% poloxamer 188 control:
  Polysorbate 20 (2%)
  Polyvinylpyrrolidone (2%)
  Polyvinylpyrrolidone (2%) and sodium deoxycholate (1%)
  Polyvinylpyrrolidone (2%) and polysorbate 20 (2%)
  Polyvinyl alcohol, partially hydrolyzed (5%)

After 12 hours of milling, the polysorbate preparation showed faster milling than the control with good uniformity. The polyvinylpyrrolidone preparation showed the presence of non-crystalline particles, possibly aggregates or residuals of polyvinylpyrrolidone, which did not significantly affect the particle-size distribution measurements, but which were visible by light microscopy. The polyvinyl alcohol preparation did not produce significant size reduction, likely due to the viscosity of the dispersant. The two-component polyvinylpyrrolidone preparations showed significant aggregates, but it was decided that the polyvinylpyrrolidone/sodium deoxycholate preparation might prove to be useful with additional development.

The polyvinylpyrrolidone and polysorbate 20 preparations, along with a modified polyvinylpyrrolidone (1%) and sodium deoxycholate (0.5%) suspensions were used in a lyophilization development experiment involving the following cryoprotectants:
  Sorbitol (10%)
  Sucrose (10%)
  Trehalose (10%)
  Mannitol (5%
  Mannitol (5%)
  Sorbitol (5%) and mannitol (2.5%)
  Sucrose (5%) and mannitol (2.5%)

Lyophilization was done at −36° C./100 mTorr and −15° C./500 mTorr with a −15° C. annealing step. Upon resuspension, only the 10% sucrose preparation gave suitable particle size recovery. Additional suspension was milled using the 1% polyvinylpyrrolidone/0.5% sodium deoxycholate preparation, but with a citrate buffer included to maintain the pH at around 7.0. Although the milled suspension preparation gelled reversibly on standing, it was combined with the following cryoprotectants:
  Sucrose (15%)
  Sucrose (10%) at 25 mg/mL BC2059
  Sorbitol (10%)
  Lactose (5%)
  Sucrose (5%) and sorbitol (5%)

Sucrose in higher concentrations relative to the API was shown to provide the best particle-size protection and, although the formulation appeared to be susceptible to meltback, an accelerated stability study, performed at 25° C./60% RH and 40° C./75 RH, showed that the formulation had good physical stability over 4 weeks.

However, in dilution tests, the formulation was found to flocculate in the saline diluent used in administration, and the pharmacokinetic release of the polyvinylpyrrolidone/sodium deoxycholate formulation was significantly lower than that of the poloxamer formulation originally tested.

Nanosuspension Containing Poloxamer 188

200 mg/mL (20%) BC2059 was milled in poloxamer 188 and provided to a third party for lyophilization optimization. The suspension was combined with a series of cryoprotectants, listed in Table 2 below, that were used in a lyophilization experiments. Initially, the 2.5% dextran/2.5% sorbitol preparation showed the most promising particle-size retention upon reconstitution, however, after one month at 40 C/75% RH, the only preparation that had retained a nanosuspension was the undried control.

Accordingly, these tests indicated that lyophilization did not work under the conditions evaluated. This finding also indicated that surprisingly the liquid suspension was more stable than had been previously observed. The initial particle elongation was determined to be an immediate and limited phenomenon, the possible result of initial over-saturation of the dispersant causing minor reprecipitation after the cessation of milling. See Table 2 below.

TABLE 2

| Cryoprotectant System | D90 Initial (um) | D90 @ T1 M |
|---|---|---|
| None, undried | 0.239 | 0.28 |
| None, dried | 23 | 61 |
| 10% sucrose | 0.309 | 1.7 |
| 5% sucrose | 7.539 | 25 |
| 10% dextran | 0.348 | 2.7 |
| 5% dextran | 0.361 | 2.9 |
| 5% dextran + 5% sucrose | 0.352 | 8.8 |
| 2.5% dextran + 2.5% sucrose | 0.29 | 18 |
| 5% dextran + 5% sorbitol | 1.02 | 40 |
| 2.5% dextran + 2.5% sorbitol | 0.987 | 24 |

Example 8

Irradiation Feasibility

Both of the developed formulation dispersant systems (polyvinylpyrrolidone/sodium deoxycholate and the poloxamer) were used to determine the feasibility of terminal sterilization by irradiation. Samples of both were prepared for both irradiation feasibility. Samples of both formulations were provided for a parallel pharmacokinetics (PK) study in laboratory animals, for which was also provided a diluent containing poloxamer 188 to be used with the polyvinylpyrrolidone/sodium deoxycholate formulation to determine if the bioavailability of the drug was related to the poloxamer. Results of the PK study showed that bioavailability surprisingly correlated with poloxamer content.

Frozen vials of both formulations were sent for irradiation. Both gamma and e-beam irradiation were tested at both 15 and 25 kGy. Vials were to be processed under frozen conditions, but also at 5° C. as a worst-case scenario to simulate potential thawing during irradiation. Degradation was independent of temperature but appeared to correlate with dose, regardless of the type of radiation.

However, initial particle-size testing, supported by subsequent stability data, showed extensive particle aggregation. Based on previously successful freeze/thaw testing, the aggregation was attributed to irradiation; however, later freeze/thaw cycling on another suspension showed similar aggregation.

It was determined that frozen storage resulted in unpredictable aggregation and was not the choice to move forward with GLP batches. The vials had been stored in a −20 C freezer prior to irradiation, and likely exhibited differential freezing rates between vials at different locations on the shelf.

Example 9

Preclinical Production

The production of 25 mg/m L tegavivint nanosuspension was done using best-clean conditions, i.e., various controls and precautions were put in place to try to minimize microbial contamination, but without guarantee of sterility.

Preparations were made using sterile water for injection to minimize not only microbial but also pyrogenic contamination. All excipients were USP/NF grade. All product contact supplies were either sterilized by autoclave, or, if not amenable to heating, sanitized with 70% isopropanol. All exposed preparations were performed in an ISO 5 quality laminar-flow hood using aseptic handling techniques. The API that was used in the manufacture of the preclinical batches was gamma-irradiated at 30 kGy prior to use.

Example 10

Rat Test Article Preparation

A 1,600-gram (nominal) batch of tegavivint suspension was prepared for administration in a rat toxicology study.

Production began with a 200-gram batch of concentrated (200 mg/mL) BC2059 nanosuspension. 10 g of poloxamer 188 was dissolved in 150 grams of water in a 250-mL serum bottle. 200 grams of YTZ milling media were added and the bottle stoppered and sealed. Given the small batch size, the entire assembly and poloxamer solution preparation was able to be autoclaved at 121 C for 15 minutes to minimize bioburden. 40 grams of irradiated API (drug substance) was added and the bottle stoppered and sealed again. This preparation was rolled on a roller mill so that the angle of break of the cascading media was about 45 degrees, visually determined.

Because of the tendency for the formulation to fail due to the entrainment of air, it was noted that the amount of milling media used is about half of what would normally be used to process a 200-gram batch of suspension. The bottle used was also smaller than typical to minimize headspace. Milling was allowed to proceed over a weekend, and the suspension was sampled via hypodermic needle through the septum.

The particle-size distribution had a D90 of 0.23 microns and was determined to be sufficient to proceed to extraction, which was done using an autoclaved solution of 160 grams of sorbitol in 1240 grams water and a glass pressure funnel containing a 60-micron sintered glass frit. The extracted suspension was mixed and filled using a positive-displacement pipette set to 5.00 mL into autoclaved 10-mL glass vials. 295 vials were filled, stoppered, and sealed, representing a 92% yield. The batch was stored at 5° C. until use.

The nanosuspension appeared ready to be administered to rats.

Example 11

Pig Test Article Preparation

A 10,400-gram (nominal) batch of tegavivint was prepared for administration in a pig toxicology study. Production began with a 1,300-gram batch of concentrated (200 mg/mL) BC2059 nanosuspension. 65 g of poloxamer 188 was dissolved in 975 grams of water in a 2000-mL media bottle. 1000 grams of YTZ milling media were rinsed and bagged for sterilization. The media and solution were autoclaved separately and combined with 260 grams of sterilized API in the media bottle. This preparation was rolled on a roller mill so that the angle of break of the cascading media was about 45 degrees, visually determined. Milling was allowed to proceed for a total of about three days, until the particle-size distribution had a D90 of 0.33 microns and was determined to be sufficient to proceed to extraction. Two aliquots of sorbitol solution, made by dissolving 520 g of sorbitol in 4030 g of water, were autoclaved and used to extract the milled suspension, similarly to what had been done for the rat-study batch.

Difficulty was noted in extraction, as apparently unmilled or larger particle size API had clogged the 60 micron filter frit, necessitating the removal of the media and the rinsing of the frit. The extracted suspension was mixed and filled using a positive-displacement pipette set to 10.0 mL into autoclaved 10-mL glass vials. 970 vials were filled, stoppered, and sealed, representing a 93% yield. The batch was stored at 5° C. until use.

The nanosuspension appeared ready to be administered to pigs.

Example 12

Autoclaving had No Significant Effect on Degradation

In conjunction with the production of test articles for preclinical studies, two batches of tegavivint suspension were prepared: one batch made with sorbitol and one without sorbitol. Stability evaluation of these suspensions, stored at 5° C., 25° C./60% RH, and 40° C./75% RH, indicated that the suspensions were reasonably stable at all conditions.

A portion of the vials from the pig-study batch was autoclaved at 121° C. for 20 minutes using a liquid cycle and the formulation, designated as batch 515-76 and FID5910.

Stability data indicated that autoclaving had no significant effect on degradation but did appear to increase particle size.

Example 13

Engineering Studies of Nanosuspension

Several engineering batches of nanosuspension of tegavivint were prepared in anticipation of clinical manufacture, and certain alterations to the process were necessary to maintain compliance and minimize loss and contamination. Partly for reasons of safety and partly to incorporate a larger-surface-area filter for extraction purposes, the glass pressure funnel that had been used for extraction was replaced with a stainless steel inline filter housing fitted with a 55-um stainless steel filter element (Pall).

Pressurization of the extraction apparatus, which had previously used nitrogen, was performed using a peristaltic pump, as this pump was also to be incorporated into the process as a means by which to sterile filter both the diluent and dispersant rather than to autoclave them. A metered peristaltic pump unit was employed for filling the vials. Given the tendency for autoclaving to increase the particle size of the formulation, the first engineering batch (RD4050-5) was submitted for gamma irradiation.

Stability results showed minimal degradation and stability similar to previous batches.

Based on preliminary particulate testing, the formulation, as processed, contained some larger particulate that did not appear to be populous enough to significantly affect laser diffraction particle-size measurements, but was significant enough to affect USP<788> testing. To mitigate the particulate, a "polishing" filter, with a porosity small enough to retain larger particles, but not so small as to affect tegavivint assay, was proposed. However, previous attempts to filter the suspension resulted in significant assay losses. Therefore, Pall Corporation was contracted to assess some of their membranes for tegavivint nanosuspension filtration suitability.

Portions of a non-best-clean suspension were filtered using various 47-mm membranes available from Pall, with a pressure feedback pumping system that is used to determine how much material can be processed before filter clogging and failure. The following membrane types were used, and the filtrate tested for PSD and assay:

TABLE 4

| Membrane | Material | D90 (nm) | Assay (% LC) |
| --- | --- | --- | --- |
| None (unfiltered control) | N/A | 256 | 92.7 |
| HDC II, 10-micron | Polypropylene | 259 | 92.5 |
| HDC II, 6-micron | Polypropylene | 253 | 92.2 |
| Ultipleat ® 6-micron | Polypropylene | 200 | 88.1 |
| Ultipleat ® 4.5-micron | Polypropylene | 207 | 91.9 |
| Glass-fiber filter | Glass fiber | Clogged immediately, not tested | |
| Depth filter | Polypropylene | Caused visible clearing of filtrate, not tested | |
| Mini Profile ®, 5-micron | Polypropylene | 206 | 93.3 |

The 6-micron HDCII membrane was chosen as the best candidate because it showed no discernable impact on either the assay value or the particle-size distribution of the nanosuspension. However, the comparatively long lead-times of the Pall filters were a limiting factor in the timely production of clinical material. Therefore, an alternative was sought, and Sartorius 8-micron polypropylene filters were used in the manufacture of two engineering batches for use in determining bioburden for sterilization validation purposes.

Unfortunately, the assay values of the two batches were negatively affected by the filtration (80.9% LC and 91.9% LC, respectively). As they were not representative of the final clinical batch profile, the batches were discarded, and another engineering batch was processed using a Pall HDC membrane filter. This batch assayed within 90 to 110% LC and the Pall HDC filter was incorporated into the final step of the manufacturing process prior to filling of the vials.

TABLE 3

Tegavivint 25 mg/mL Engineering Lot

| | | Impurities > 0.1% | | | | | Total |
| --- | --- | --- | --- | --- | --- | --- | --- |
| | BC-2059 | RRT 0.60 (Impurity 1) | RRT 0.95 | RRT 1.08 (Impurity 2) | RRT 1.11 (Impurity 3) | RRT 1.17 (Impurity 4) | RRT 1.23 | Impurities > 0.1% |
| Unsterilized | 103.3% | 0.52 | 0.21 | 0.12 | 0.44 | 0.30 | ND | 1.6 |
| Autoclave | 103.6% | 0.53 | 0.21 | 0.12 | 0.46 | 0.32 | ND | 1.6 |
| Gamma Irradiated | 101.5% | 0.42 | 0.21 | 0.12 | 0.73 | 0.61 | 0.1 | 2.2 |

Example 14

Pharmacokinetic Study of Tegavivint Following Slow Intravenous Bolus Administration to Female Sprague-Dawley Rats The objective of this study was to investigate the pharmacokinetics of tegavivint following a single intravenous slow bolus administration of tegavivint to female Sprague-Dawley rats.

The study was performed using parallel design (n=4/group) with serial sampling, as summarized in Table 5:

TABLE 5

| Treatment | Group Number | No. of Rats | Dose (mg/kg) | Dose Volume (mL/kg) | Concentration (mg/mL) |
|---|---|---|---|---|---|
| BC2059 | G1 | 4 | 10 | 2 | 5 |

Source

Sprague-Dawley rats used in the study were obtained from In-house animal resource facility, Advinus Therapeutics Ltd., Bengaluru, India. The animals were about 10-11 weeks of age on the day of dosing.

Identification

Each animal was identified with a unique identification number indicated on the cage card and turmeric solution marking on the animal body. The cage card identified each cage with study number, identification number, species and strain, dose and gender.

Housing and Environment

Rats were acclimatized to the study area conditions for 3 days before dosing. Animals were housed (one per cage) in polypropylene cages and maintained in controlled environmental conditions with 12 h light and 12 h dark cycles. The temperature and humidity of the room was maintained between 22±3° C. and 40-70%, respectively. The room underwent 10-15 fresh air change cycles per hour.

Food and Water

The experimental animals were provided ad libitum of standard pelleted food (Teklad Certified (2014C) Global 14% Protein Rodent Maintenance Diet-Rodent pellet food, manufactured by Harlan Laboratories B.V Maasheseweg 87c PO Box 553, 5800, AN Venray, The Netherlands.

Dose Preparation and Administration

The stock formulation (25 mg/mL) was provided. Accurately, 600 µL of dose formulation (Stock, 25 mg/mL) was transferred to labeled glass container. To this, 2.4 mL of 5% dextrose solution was added, vortex mixed and sonicated to obtain homogeneous suspension of 5 mg/mL strength. Animals were dosed under fed condition. Rats were administered a single dose of 10 mg/kg of tegavivint by slow intravenous bolus (over 1.5 min) jugular vein catheter using 1 mL BD syringe guided with 23 G blunt needle at a dose volume of 2 mL/kg. Syringes used for dosing were weighed before and after dose administration in order to calculate the actual dose administered.

Sample Collection and Processing

Blood samples were collected at 0.083, 0.25, 0.5, 1, 2, 4, 6, 8, 12 and 24 h post dose. At each time point, approximately, 0.25 mL of blood was withdrawn from jugular vein of the cannulated rat and transferred to a labeled microfuge tube containing 200 mM $K_2EDTA$ (20 µL per mL of blood). Following sampling, equal volume of heparinized saline was replaced into the catheter. The blood samples were kept on wet ice at all times immediately after collection and the plasma was separated by centrifugation at 5000 g for 5 minutes at 4±2° C. The plasma samples were separated within 1 h of scheduled time and stored below −60° C. until bioanalysis.

Bioanalysis

Bioanalysis was performed using fit-for-purpose LC-MS/MS method for the quantification of BC2059 in rat plasma samples. The calibration curve (CC) for the method consisted of at least 6 non-zero calibration standards along with a blank and blank with internal standard samples with a lower limit of quantification (LLOQ) of 0.050 µg/mL. Study samples were analyzed along with three sets of quality control samples (9 QC samples; low, medium and high QC samples in triplicate).

Pharmacokinetic Data Analysis

The pharmacokinetic parameters for tegavivint were calculated using the non-compartmental analysis tool (extra vascular) of the validated Phoenix® WinNonlin® software (version 6.3). The area under the concentration time curve (AUClast and AUCinf) was calculated by linear trapezoidal rule. The C0 (back extrapolated concentration at time zero) was estimated following intravenous bolus dose administration by back-extrapolating the first two concentration values. The total plasma clearance (CL) and volume of distribution at steady-state (Vss) were estimated values. The elimination rate constant value (k) was calculated by linear regression of the log-linear terminal phase of the concentration-time profile using at least 3 declining concentrations in terminal phase with a correlation coefficient of >0.8. The terminal half-life value (T½) was calculated using the equation 0.693/k. The alpha and beta half-lives were calculated and reported.

Experimental Results

Following single slow intravenous bolus administration of tegavivint (Dose: 10 mg/kg) to rats, the mean plasma clearance (CL) was estimated to be 9.92 mL/min/kg, which is about 5.5-fold lower than the normal rat liver blood flow of 55 mL/min/kg. The mean plasma volume of distribution at steady state (Vss) was found to be almost 9.34-fold greater than the normal body water of 0.7 L/kg, possibly suggesting wide distribution into tissue compartments. The semi log plasma concentration-time plots indicate that BC2059 exhibited bi-exponential elimination pattern with rapid distribution half-life (T½ alpha) of 0.546 h and long terminal plasma half-life (T½ beta) of 13.8 hours.

TABLE 6

PK Characteristics of BC2059

| CL (mL/min/kg) | $V_{ss}$ (L/kg) | $C_0$ (µg/mL) | $AUC_{last}$ (µg · h/mL) | $AUC_{inf}$ (µg · h/mL) | $MRT_{last}$ (h) | $T_{1/2}$ Alpha (h) | $T_{1/2}$ Beta (h) |
|---|---|---|---|---|---|---|---|
| 9.92 ± 1.79 | 6.54 ± 3.07 | 62.2 ± 7.13 | 14.6 ± 3.69 | 17.2 ± 3.29 | 4.07 ± 0.579 | 0.546 ± 0.0686 | 13.8 ± 3.11 |

Regression points 0.5, 1 and 2 h for alpha phase and 6, 8, 12 and 24 h for terminal beta phase were selected to calculate elimination rate constant.

Example 15

A Dose-Escalating Intravenous Infusion Study of Tegavivint in Male Beagle Dogs

Study Animals: Four male non-naïve Beagle dogs were released by Xenometrics for study use on Apr. 20, 2017. The animals were fed Harlan Teklad® Global 25% Protein Certified Dog Diet 2025C ad libitum throughout the study (except for brief periods during in-life procedures when it was Dosing: Animals were dosed via intravenous (IV) infusion (via jugular vein) for 4 hours (h) [±5 minutes (min)].

TABLE 7

Study Dosing Summary

| Dose Number | Dosing Day | Test Article | Dose (mg/kg) | Concentration (mg/mL) | Infusion Rate (mL/kg/hour) |
|---|---|---|---|---|---|
| 1 and 2 | 1 and 3 | BC-2059 in Poloxamer 188 and sorbitol; 5% dextrose as the diluent | 5 | 1 | 1.25 |
| 3 and 4 | 5 and 8 | | 10 | 2 | 1.25 |
| 5 and 6 | 12 and 16 | | 15 | 2 | 1.88 |

Pharmacokinetic (PK) Blood Collection:

Blood samples were collected on the last dosing day (Dose 6; 15 mg/kg) prior to start of infusion and at 4, 12, 24, 36, 48, and 72 h after the start of infusion. All blood samples were collected within 10 minutes of the target time and processed per protocol. Bioanalytical results indicated tegavivint was present in all plasma samples.

TABLE 8

Calculated Plasma BC-2059 Values (ng/mL) in Beagle Dogs Following a 15 mg/kg 4 h IV Infusion

| Animal No. | Timepoint (h Postdose) | | | | | | | |
|---|---|---|---|---|---|---|---|---|
| | Predose | 4 | 12 | 24 | 36 | 48 | 72 | 96 | 120 |
| JY1001 | 404 | 1310 | 916.0 | 1120 | 834 | 663 | 511 | 360 | 321 |
| JY1002 | 309 | 1320 | 1050 | 1120 | 931 | 656 | 480 | 310 | 262 |
| JY1003 | 284 | 1150 | 777 | 1070 | 708 | 647 | 524 | 364 | 281 |
| JY1004 | 257 | 1600 | 784 | 723 | 674 | 664 | 393 | 277 | 228 |

The pharmacokinetic parameters were determined for BC-2059 following the final 15 mg/kg infusion of the drug over 4 h. The mean values are presented in Table 8 above. The data indicate a half-life of 53.0 h and an overall $AUC_{0-120h}$ of 73480 ng*h/mL.

TABLE 9

Mean PK Parameters for BC-2059

| Dose (mg/kg) | Route | Cmax (ng/mL) | $AUC_{0-120\,h}$ (h*ng/mL) | T½ (h) |
|---|---|---|---|---|
| 15 | IV over 4 h | 1345 ± 187 | 73480 ± 5803 | 53.0 ± 6.7 | n = 4 males

Example 16

Nebulizing Delivery of Tegavivint Formulations

The purpose of this experiment was to test nebulized delivery of nanosuspensions. This experiment demonstrated that nebulized delivery was successful.

Tegavivint particles suspended in Poloxamer 188/sorbitol at a concentration of 25 mg/mL were used.

These formulations were applied to the mice in the form of aerosols, through the method of whole body exposure. The mice were placed inside a plastic box. This box was sealed and connected by one of its sides to the outlet of the nebulizer device, and on the other side to a system of closed water. The whole procedure was carried out inside the fume hood of the animal room.

For the first experiment, the nebulizer kit of SATER LABS was used. This device uses the jet system. The device was primed with 5 ml of the drug, i.e. 125 mg of tegavivint (BC2059), for each group of 5 mice, and then the device was connected to the power source for nebulization. The energy was supplied by a DeVilbiss compressor model 646, which allows 5-7 pounds of pressure, and a flow of 6-8 liters per minute. For the second experiment, the device used was the Altera, ultrasonic nebulizer.

For the two experiments, 10 male bcat-Ex3 mice were used for each set. These mice were separated into 2 groups of 5 mice each. The first group received the drug daily, for 5 consecutive days. The second group received the drug only once (the fifth day). On day 5 all mice were sacrificed, lung harvested, and samples were stored at −30 degrees, in two labeled nylon bags, each containing the 5 samples from each group.

Results:

TABLE 10

| Label | Group ID | Animal ID | Matrix/ Bleed time | Analyte | Lung Concentration (ng/mL) | Lung Concentration (ng/g) |
| --- | --- | --- | --- | --- | --- | --- |
| Aerosol 1 Day #1-1 Oct. 10, 2017 | 2 | 1 | Mouse lung | BC2059 | 14200 | 56800 |
| Aerosol 1 Day #2-2 Oct. 10, 2017 | 2 | 2 | Mouse lung | BC2059 | 1300 | 5200 |
| Aerosol 1 Day #3-3 Oct. 10, 2017 | 2 | 3 | Mouse lung | BC2059 | 4270 | 17100 |
| Aerosol 1 Day #4-4 Oct. 10, 2017 | 2 | 4 | Mouse lung | BC2059 | 1260 | 5040 |
| Aerosol 1 Day #5-5 Oct. 10, 2017 | 2 | 5 | Mouse lung | BC2059 | 4190 | 16800 |
| Aerosol 5 Day #1-6 Oct. 10, 2017 | 3 | 6 | Mouse lung | BC2059 | 4640 | 18600 |
| Aerosol 5 Day #2-7 Oct. 10, 2017 | 3 | 7 | Mouse lung | BC2059 | 1650 | 6600 |
| Aerosol 5 Day #3-8 Oct. 10, 2017 | 3 | 8 | Mouse lung | BC2059 | 3620 | 14500 |
| Aerosol 5 Day #4-9 Oct. 10, 2017 | 3 | 9 | Mouse lung | BC2059 | 3080 | 12300 |
| Aerosol 5 Day #5-10 Oct. 10, 2017 | 3 | 10 | Mouse lung | BC2059 | 3550 | 14200 |
| Nebulizer 1 Day #1-11 Oct. 10, 2017 | 4 | 11 | Mouse lung | BC2059 | 2840 | 11400 |
| Nebulizer 1 Day #2-12 Oct. 10, 2017 | 4 | 12 | Mouse lung | BC2059 | 2910 | 11600 |
| Nebulizer 1 Day #3-13 Oct. 10, 2017 | 4 | 13 | Mouse lung | BC2059 | 8660 | 34600 |
| Nebulizer 1 Day #4-14 Oct. 10, 2017 | 4 | 14 | Mouse lung | BC2059 | 3780 | 15100 |
| Nebulizer 1 Day #5-15 Oct. 10, 2017 | 4 | 15 | Mouse lung | BC2059 | 601 | 2400 |
| Nebulizer 5 Day #1-16 Oct. 10, 2017 | 5 | 16 | Mouse lung | BC2059 | 4770 | 19100 |
| Nebulizer 5 Day #2-17 Oct. 10, 2017 | 5 | 17 | Mouse lung | BC2059 | 4290 | 17200 |
| Nebulizer 5 Day #3-18 Oct. 10, 2017 | 5 | 18 | Mouse lung | BC2059 | 4690 | 18800 |
| Nebulizer 5 Day #4-19 Oct. 10, 2017 | 5 | 19 | Mouse lung | BC2059 | 3040 | 12200 |
| Nebulizer 5 Day #5-20 Oct. 10, 2017 | 5 | 20 | Mouse lung | BC2059 | 5730 | 22900 |

LLOQ: 20.0 ng/g
"Aerosol" refers to standard aerosol jet nebulizer (Safer Labs);
"Nebulizer" refers to nebulizer ultrasonic eRapid machine (Altera)
"1 Day" refers to single-dose on Day 5;
"5 Day" refers to 5 daily doses on Days 1-5.

Example 17

Pig Studies with Liquid Formulation of Tegavivint and Nanosuspension of Tegavivint Liquid Suspension was Poorly Tolerated by Pigs Tegavivint was intravenously administered to minipigs in a series of pharmacokinetic studies to determine a formulation that would be suitable for GLP toxicology studies, both in terms of systemic exposures and in tolerability to the drug product formulation. These studies were all conducted at Sinclair Research (Auxvasse, Mo.).

In the first study, the drug was obtained in a formulation consisting of Tween 80, ethanol, polyethylene glycol (PEG) and vitamin E TGPS (d-alpha tocophenyl polyethylene glycol 1000 succinate). This stock formulation was diluted in 20% Intralipid® (phospholipid stabilized soybean oil) to the final dose concentration. Two pigs were administered 1.7 mg/kg over 6 h and two pigs were administered 2.2 mg/kg over 24 h. The formulation provided good systemic exposures.

Comparing dose normalized values the shorter 6 h duration, relative to the 24 h duration, resulted in higher peak concentrations ($C_{max}$/Dose) at the end of the infusion as the total dose was given over a shorter duration. However, the overall systemic exposures over time (AUCs/Dose) were similar between the two infusion durations, meaning that with a longer infusion time, it was possible to obtain similar overall systemic exposures while avoiding higher peak plasma concentrations.

However, while good systemic exposures were observed with this formulation, marked infusion reactions were observed, and this formulation was not tolerated by minipigs either over a 6 h or a 24 h infusion period. It was hypothesized that the tween/ethanol/PEG/Vitamin E/Intralipid solvent-based excipients and probable drug precipitation were responsible for the infusion reactions and not tegavivint itself. Indeed, tegavivint does not cause hemolysis of red blood cells either when in the nanoparticle form or when dissolved in DMSO.

Lyophilized Nanosuspensions of Tegavivint were Better Tolerated but Ultimately were Abandoned Due to Stability Issues In the subsequent study, tegavivint was milled to a nanoparticle size and a non-solvent formulation was used. In this study, Study B01-109, a lyophilized form of tegavivint was obtained and reconstituted in water to provide a stock formulation consisting of a suspension of tegavivint 10 mg/mL, 2.5 mg/mL Poloxamer 188 and 5 mg/mL sorbitol. This stock solution was diluted with normal saline to the final requisite concentrations for intravenous administration. Two pigs were infused with 2.9 mg/kg and 2 pigs were infused with 12.3 mg/kg over a 4 h infusion. One pig in the 12.1 mg/kg dose group had very high systemic exposures. Notwithstanding this pig, dose normalized AUC, and to a lesser extent the $C_{max}$, were dose linear across the 2.8 to 12.1 mg/kg dose given over the same duration. With the exception of the one pig in the 12.1 mg/kg dose group, the dose normalized exposures were less with this lyophilized form of nano-milled tegavivint compared to the tween/ethanol/PEG/Vitamin E/Intralipid solvent-based formulation used in Study B01-107.

Nevertheless, as this formulation was well-tolerated by the minipigs with none of the infusion reactions observed in Study B01-107, the lyophilization process was scaled up for future work. However, in the scale-up process, we were unable to obtain a lyophilized product with adequate stability and an alternative lyophilized formulation of tegavivint was needed.

In Study TXPK-006-2059-24 h, a lyophilized formulation of milled tegavivint was used. The lyophilized formulation used was reconstituted in water to final concentrations of BC2059 25 mg/mL, 0.125% polyvinylpyrrolidone (PVP), 0.0625% NaDeoxycholate (NaDOC) and 10% sucrose. This bulk solution was diluted in normal saline to the requisite concentrations for dose administration to two pigs per treatment group at 12.3 or 49.2 mg/kg over a 24 h infusion. Test article flocculation was observed in the syringes and the syringes were agitated throughout the 24 h infusion period. Nonetheless, systemic exposures were exceedingly low compared to Studies B01-107 and B01-109. Subsequent formulation work showed that saline with this lyophilized formulation resulted in test article aggregation and an ionic (saline) diluent could not be used.

Frozen Liquid Nanosuspensions of Tegavivint Worked

At this point, lyophilization was abandoned and frozen liquid formulations of the milled tegavivint were investigated. In Study TXPK-001-2059-pig 24 h PK, three minipigs were assigned one per group to one of three groups with the formulations administered over 24 h. Two frozen milled suspensions were provided by Particle Sciences. BC2059-1 was a 25 mg/mL BC2059, 0.125% PVP, 0.0625% NaDOC, 10% sucrose, suspension (Batch no. 515-10) and BC2059-2 was a 25 mg/mL BC2059, 0.625% poloxamer 188, 10% sorbitol, suspension (Batch no. 515-13). The diluent for both of these formulations was D5W. A third group was the BC2059 PVP/NaDOC/sucrose frozen formulation BC2059-1 with a poloxamer 188/saline diluent to investigate a possible role for the poloxamer 188 in systemic exposures.

Of these 3 frozen test article formulations, the 25 mg/mL tegavivint, 0.625% poloxamer 188, 10% sorbitol, nanosuspension diluted with D5W showed the highest systemic exposures. The dose normalized AUC for this formulation was somewhat less than the dose normalized exposures observed in the 24 h infusions in Study B01-107, but not markedly so. The dose normalized exposures were considerably higher than observed in 3 of 4 pigs in Study B01-109, indicating that the saline diluent in that study might have affected systemic exposures with the lyophilized poloxamer 188 formulation of BC2059, albeit to a much lesser extent than observed with the PVP/NaDOC formulation of tegavivint.

TABLE 11

Single-Dose Pharmacokinetics of BC2059 in the Minipig

| Study | Formulation and Infusion Duration | Actual Dose (mg/kg) | Cmax (ng/mL) | Cmax/ Dose | AUC (ng*h/mL) | AUC/ Dose |
|---|---|---|---|---|---|---|
| B01-107 | BC2059-13[a] 6h | 1.7 | 1800, 940 | 1059, 553 | 7960, 5395 | 4682, 3174 |
| | BC2059-13[a] 24 h | 2.2 | 270, 1120 | 123, 509 | 5544, 12889 | 2520, 5859 |
| B01-109 | BC2059[b] 4 h | 2.8 | 448, 540 | 160, 193 | 2144, 2417 | 766, 863 |
| | BC2059[b] 4 h | 12.1 | 26100, 4690 | 2157, 388 | 28778, 11617 | 2378, 960 |
| TXPK-006-2509-24 h pig tol | BC2059[c] 24 h | 12.3 | 30, 23 | 3, 2 | 506, 360 | 43, 31 |
| | BC2059[c] 24 h | 49.2 | 91, 106 | 2, 2 | 1526, 1719 | 31, 35 |
| TXPK-001-2059-pig 24 PK | BC2059-1[d], 24 h | 47 | 2860 | 61 | 16269 | 346 |
| | BC2059-2[e], 24 h | 53 | 4370 | 82 | 78893 | 1489 |
| | BC2059-3[f], 24 h | 51 | 2590 | 41 | 49645 | 973 |

[a]20 mg/mL BC2059 in 30% Ethanol, 50% PG, 10% Tween 80, and 10% D-α-Tocopherol polyethylene glycol 1000 succinate (Lot P492-01); values reported for 2 minipigs
[b]10 mg/mL BC2059, 2.5 mg/mL Poloxamer 188 and 5 mg/mL sorbitol (Lot No. BET 1213-001-29); values reported for 2 minipigs
[c]25 mg/mL BC2059, 0.125% PVP, 0.0625% NaDOC and 10% sucrose (Lot No. BET 1213-001-49); values reported for 2 minipigs
[d]25 mg/mL BC2059, 0.125% PVP, 0.0625% NaDOC, 10% sucrose, nanosuspension (Lot 515-10) diluted to 2 mg/mL final concentration in dextrose 5%; single minipig
[e]25 mg/mL BC2059, 0.625% poloxamer 188, 10% sorbitol, nanosuspension (Lot 515-13) diluted to 2 mg/mL final concentration in dextrose 5%; single minipig
[f]25 mg/mL BC2059, 0.125% PVP, 0.0625% NaDOC, 10% sucrose, nanosuspension (Lot 515-10) diluted to 2 mg/mL final concentration in poloxamer 188/saline to a final concentration of 0.05% poloxamer; single minipig Based on the results of these single dose infusion studies in minipigs, the formulation selected for repeated 2-dose toxicology studies was the frozen formulation of 25 mg/mL BC2059 with 0.625% poloxamer 188, 10% sorbitol (nanosuspension) and diluted with D5W During the conduct of the 2-dose non-GLP studies to support dose selection for the IND-enabling GLP toxicology studies, we learned in the scale-up process and production of Particle Sciences Batch no. 515-33 that freezing of the formulation resulted in aggregation of tegavivint in the vials.

Given this aggregation with freezing, we subsequently made the decision to pursue the 25 mg/mL nano-milled BC2059 in 0.625% poloxamer 188, 10% sorbitol formulation holding at 2-4° C. Aggregation was not observed in multiple lots of the milled BC2059 suspension, provided the formulation was not frozen. The poloxamer/sorbitol formulation, refrigerated at 2-4° C., was used for the IND-enabling GLP toxicology studies and in the non-GLP beagle dog study.

Example 18

Efficacy of Nebulized Tegavivint in a Mouse Model of Idiopathic Pulmonary Fibrosis The purpose of this experiment was to investigate tegavivint nanosuspension in a mouse model of bleomycin-induced idiopathic pulmonary fibrosis (IPF). Test articles were as follows:

Tegavivint (BC2059) in a nano-milled suspension 25 mg/mL in 0.625% poloxamer 188 and 10% sorbitol. The test article was refrigerated at about 4° C.

Nebulizing equipment was Altera ultrasonic eRapid machine nebulizer (model #678G1002).

Animals were 8-12 week old C57BL/6 male mice (Jackson Lab, Bar Harbor, Me.).

Experimental Procedure

TABLE 12

| Group | # of mice | Day 0 | Day 5-21 |
|---|---|---|---|
| 1 | 4 | IT PBS 50 µl | 5 ml of Vehicle (0.625% poloxamer 188/10% sorbitol) aerosol, BID |
| 2 | 4 | IT Bleomycin 0.025 U in 50 µl saline | 5 ml of Vehicle (0.625% poloxamer 188/10% sorbitol) aerosol, BID |
| 3 | 5 | IT Bleomycin 0.025 U in 50 µl saline | 5 ml of 25 mg/ml tegavivint aerosol, BID |

Murine model of pulmonary fibrosis was induced by intratracheally (IT) injected bleomycin (APP Pharmaceuticals, Schaumburg, Ill.). One dose of 0.025 U bleomycin dissolved in 50 microliters of Saline 0.9%, or PBS as control was administered to each animal on day 0.

Tegavivint nanosuspension was applied to Group 3 in the form of aerosols, through the method of whole body exposure. The mice were placed inside a plastic box. This box was sealed and connected by one of its sides to the outlet of the nebulizer device, and on the other side to a system of closed water. The whole procedure was carried out inside the fume hood of the animal room. In each treatment session, 5 ml of 25 mg/ml Tegavivint (125 mg) was nebulized over 15 min to each group of 4-5 mice in the chamber. To increase exposure of the mice to the aerosol, Tegavivint that precipitated in the aerosol chamber was collected with a syringe and re-nebulized a second and a third time. Mice were nebulized twice a day between day 5 and day 21 after administration of bleomycin. Group 1 and 2 received nebulized vehicle 5 ml in the same manner.

The body weight of animals was recorded on Days 0, 5, 8, 12, 16, 19, and 21.

Measurements of lung mechanics were performed on Day 21 as previously described (Morales-Nebreda L, et al. AJRCMB 2015) on Day 21 using a FlexiVent mouse ventilator (Scireq, Montreal, PQ, Canada) according to the protocols established by Scireq. A standard ventilation history for each mouse was obtained with three total lung capacity maneuvers before the forced oscillation and quasistatic pressure-volume curve protocols that were used to calculate airway resistance, dynamic and quasistatic tissue compliance, and elastance.

On Day 21 all animals were sacrificed and lungs were harvested. Total lung collagen content was evaluated using the Hydroxyproline Assay as previously described (Morales-Nebreda L, et al. AJRCMB 2015). In brief, mouse lungs were harvested and suspended in 1 ml of 0.5 M acetic acid and then homogenized, first with a tissue homogenizer (60 s on ice) and then using 15 strokes in a Dounce homogenizer (on ice). The resulting homogenate was spun (12,000×g) for 10 minutes, and the supernatant was used for subsequent analyses. Collagen standards were prepared in 0.5 M acetic acid using rat tail collagen (Sigma-Aldrich, St. Louis, Mo.). Picrosirius red dye was prepared by mixing 0.2 g of Sirius red F3B (Sigma-Aldrich) with 200 ml of water; 1 ml of the Picrosirius red dye was added to 100 µl of the collagen standard or the lung homogenates and then mixed continuously at room temperature on an orbital shaker for 30 minutes. The precipitated collagen was then pelleted and washed once with 0.5 M acetic acid (12,000×g for 15 min each). The resulting pellet was resuspended in 1 ml of 0.5 M NaOH and Sirius red staining was quantified spectrophotometrically (540 nm) using a colorimetric plate reader (Bio-Rad, Hercules, Calif.).

Results

Group 2 showed statistically significant body weight reduction after bleomycin treatment, which is one of the indicators of IPF induction. In contrast, inhaled tegavivint treatment in Group 3 reversed the body weight loss caused by the bleomycin induced lung injury.

TABLE 13

| | Change in body weight (%) | | |
|---|---|---|---|
| Animal # | Group 1 | Group 2 | Group 3 |
| 1 | 3.24 | −10.85 | −2.83 |
| 2 | 9.13 | −1.25 | 5.2 |
| 3 | 9.85 | −4.67 | 7.3 |
| 4 | 12 | −2.62 | 7.3 |
| 5 | | | 7.9 |

Further, bleomycin induced decreased lung compliance in Group 2, which indicates the induction of fibrosis. Inhaled tegavivint treatment after bleomycin injury in Group 3 reversed the compliance values to near those of the sham-treated controls in Group 1.

TABLE 14

| | Compliance (ml/cm H$_2$0) | | |
|---|---|---|---|
| Animal # | Group 1 | Group 2 | Group 3 |
| 1 | 0.076337 | 0.044172 | 0.055153 |
| 2 | 0.068275 | 0.042324 | 0.056036 |
| 3 | 0.058057 | 0.048667 | 0.067618 |

TABLE 14-continued

| | Compliance (ml/cm H₂0) | | |
|---|---|---|---|
| Animal # | Group 1 | Group 2 | Group 3 |
| 4 | 0.07324 | 0.042422 | 0.054295 |
| 5 | | | 0.056101 |

Further, the total lung collagen content as measured by the Hydroxyproline assay showed marked increase in Group 2, indicating active fibrosis after bleomycin injury; in contrast, inhaled tegavivint treatment after bleomycin injury in Group 3 reversed this change and the collagen levels are closed to sham-treated controls in Group 1.

TABLE 15

| | Hydroxyproline (μg/half lung) | | |
|---|---|---|---|
| Animal # | Group 1 | Group 2 | Group 3 |
| 1 | 51.296 | 75.632 | 70.016 |
| 2 | 36.32 | 85.824 | 39.44 |
| 3 | 44.432 | 68.768 | 45.68 |
| 4 | 37.568 | 77.504 | 58.784 |
| 5 | | | 64.296 |

Thus, this experiment demonstrated that tegavivint has a great potential to treat IPF.

Example 19

Assessing Aerosolized Tegavivint Formulations

A series of BC-2059 (tegavivint) formulations were aerosolized using vibrating mesh and compressed air nebulizers to determine the most efficient method of aerosol generation. The aerosols were characterized for aerosol concentration and particle size distribution in a rodent nose-only exposure chamber. Each formulation had different variables adjusted to assess impact on aerosol performance. These included particle size reduction of the API, excipient profile and nebulizer utilized.

The objective of this study was to determine a method by which test article BC-2059 could be aerosolized for inhalation studies for rodents.

Test article BC-2059 was suspended in 0.1% Tween 80 in purified water at a concentration of 15 mg/mL. The suspension was sonicated using a Covaris S220x Ultrasonicator (Covaris, Boston Mass.) and then mixed on a vortex for one minute. Sonication and mixing by vortex was repeated a total of 15 times.

The remaining bulk BC-2059 powder was ground in a Planetary Ball Mill (Retsch, Germany) for 10 minutes at 150 RPMs utilizing a 12 mL ball mill jar and three metal balls. The milled BC-2059 powder was suspended in 0.1% Tween 80 in purified water at a concentration of 15 mg/mL. The suspension was sonicated using the procedure outlined above.

The remaining bulk BC-2059 powder was ground in a Planetary Ball Mill (Retsch, Germany) for 60 minutes at 300 RPMs utilizing a 12 mL ball mill jar and three metal balls. The milled BC-2059 powder was suspended in 0.1% Tween 80 in purified water and 10% PEG 400 in purified water at a concentration of 15 mg/mL. The suspensions were sonicated using the procedure outlined above. An additional 15 mg/mL BC-2059 suspension using 10% ethanol in purified water was prepared. The suspension was sonicated for 10 minutes using a VWR sonicator (VWR, Radnor Pa.) and mixed for 4 minutes using a vortex mixer.

An additional formulation (nanomilled suspension of 25 mg/mL BC-2059 in 0.625% poloxamer 188 and 10% sorbitol) was used as received without further modification.

The aerosols were generated from formulations prepared with a series of surfactants with 4 separate nebulizers (Aeroneb Solo (Aerogen, Ireland), Pari LC Plus (Pari Respiratory Equipment Inc. Midlothian Va.), Hospitak Up Mist, Hospitak Inc. Farmdale, N.Y.), and Hudson Micro-Mist (Teleflex Inc. Research Triangle Park, N.C.) and transitioned into a 2 tier flow-past rodent exposure system.

The total concentration of aerosol in the exposure atmosphere was determined by the analysis of filter samples (GF/A 47-mm filters). Filter samples were collected at a nominal flow rate of 0.3 L/min. Filter samples collected throughout the study were analyzed gravimetrically to determine the total aerosol concentration, and submitted for HPLC analysis.

Filters with test article were extracted in 1:1 acetonitrile: methanol and analyzed by the HPLC-UV assay.

Particle size distribution (PSD) of the test article was measured at the breathing zone using an In Tox, mercer style cascade impactor.

Results

The aerosol concentrations (gravimetric and chemical) are shown in Table 16 below.

TABLE 16

Method Development Summary

| API PSD Reduction | Excipients | Formulation Conc. (mg/mL) | Nebulizer | Total Aerosol Conc. (mg/L) | BC-2059 Aerosol Conc. (μg/L) |
|---|---|---|---|---|---|
| Covaris | 0.1% Tween 80 | 15.04 | Aeroneb Solo | 0.247 | 1.3 |
| Covaris and Ball Mill (60 min) | 0.1% Tween 80 | 15.06 | Hospitak | 0.229 | 66 |
| Covaris and Ball Mill (10 min) | 0.1% Tween 80 | 15.58 | Pari LC Plus | 0.123 | N/A |
| Covaris and Ball Mill (60 min) | 0.1% Tween 80 | 15.08 | Hudson MicroMist | 0.093 | 86 |
| Sonicator and Ball Mill (60 min) | 10% Ethanol | 15.00 | Hudson MicroMist | 0.027 | 20.2 |
| Covaris and Ball Mill (60 min) | 10% PEG-400 | 15.08 | Hudson MicroMist | 2.58 | 7.2 |
| Tegavivint BC2059 nano-milled suspension | 0.625% poloxamer 188/10% sorbitol | 25.0 | Hudson MicroMist | 2.47 | 484 |

Particle size for test atmospheres was measured using an In-Tox Cascade impactor for suspensions prepared with 0.1% Tween 80 in ultrapure water, and the sponsor provided poloxamer suspension using a compressed air nebulizer. The mass median aerodynamic diameter and geometric standard deviation for each formulation are listed in Table 17 below. Particle size distributions are shown in FIG. 1 and FIG. 2.

TABLE 17

| Particle Size Distribution | | | | | | |
|---|---|---|---|---|---|---|
| API PSD Reduction | Excipients | Formulation Conc. (mg/mL) | Nebulizer | MMAD | GSD | $R^2$ |
| Covaris and Ball Mill (60 min) | 0.1% Tween 80 | 15.06 | Hospitak | 1.26 | 2.21 | 0.99 |
| Tegavivint BC2059 nono-milled suspension | 0.625% poloxamer 188/10% sorbitol | 25.0 | Hudson μmist | 2.46 | 1.45 | 0.98 |

CONCLUSION

Formulations of BC-2059 were nebulized and introduced to nose-only inhalation exposure chamber. The exposure atmospheres were characterized for aerosol concentration using gravimetric and HPLC assay. The highest gravimetric aerosol concentration was measured at 2.47 mg/L for the poloxamer formulation, which corresponded to 0.48 mg/L of active test article. The particle size distribution for this formulation was measured by cascade impactor and had a MMAD of 2.46 μm with a geometric standard deviation of 1.45 μm.

In reviewing the poloxamer formulation results against the previous results, the aerosol concentration of 0.484 mg/L of BC2059 would result in a 1.5 mg/kg pulmonary deposited dose (10% DF) to a 30 gram mouse in 30 minutes. Based on standard mouse lung weights, this would result in 0.2 mg/g in the lung tissue. The previous testing resulted in 0.02 mg/g (assayed concentration).

Therefore, this BC2059 nanomilled suspension which was nebulized gave the most optimal concentration in the aerosol in comparison to the other BC2059 formulations.

What is claimed is:

1. A composition comprising:

a. 25 mg/ml of tegavivint or a pharmaceutically acceptable salt, ester, amide, stereoisomer or geometric isomer thereof;

b. 0.625% Poloxamer 188; and c. 10% sorbitol;

wherein tegavivint or the pharmaceutically acceptable salt, ester, amide, stereoisomer or geometric isomer thereof is in the form of a nanosuspension comprising particles of tegavivint or the pharmaceutically acceptable salt, ester, amide, stereoisomer or geometric isomer thereof, and wherein the particles have an effective D50 of less than or equal to 500 nm and D90 of less than or equal to 1.0 micrometer (μm) when measured using laser diffraction, wherein the percentages are by weight of the composition.

2. The composition of claim 1, wherein said composition is prepared by milling.

3. The composition of claim 1, wherein said composition is prepared by LyoCell technology.

4. A process of preparing a composition comprising:

a) mixing particles of tegavivint or a pharmaceutically acceptable salt, ester, amide, stereoisomer or geometric isomer thereof; with a Poloxamer 188 surfactant and an acceptable carrier to produce a suspension;

b) roller milling or using a high energy mill to mill the suspension of step (a); and c) adding sorbitol to the particles of step (b)

to produce a formulation comprising 25 mg/ml of tegavivint or a pharmaceutically acceptable salt, ester, amide, stereoisomer or geometric isomer thereof; 0.625% Poloxamer 188; and 10% sorbitol;

wherein tegavivint or the pharmaceutically acceptable salt, ester, amide, stereoisomer or geometric isomer thereof is in the form of a nanosuspension comprising particles of tegavivint or the pharmaceutically acceptable salt, ester, amide, stereoisomer or geometric isomer thereof, and wherein the particles have an effective D50 of less than or equal to 500 nm and D90 of less than or equal to 1.0 micrometer (μm) when measured using laser diffraction, wherein the percentages are by weight of the composition.

5. The process of claim 4, wherein the composition exhibits long term stability.

6. The composition of claim 1, wherein the composition is formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration; or (d) any combination of (a), (b), and (c).

7. A method of ameliorating cancer or tumor metastasis in a mammal in need thereof comprising administering to said mammal an effective amount of the composition of claim 1.

8. A method for ameliorating cancer comprising administering to a subject in need thereof a combination of: 1) a pharmaceutically effective amount of the nanoparticulate composition of claim 1; and 2) a pharmaceutically effective amount of at least one additional anti-cancer agent.

9. The method of claim 8, wherein the additional anti-cancer agent is selected from the group consisting of anti-mitotic agents, antimetabolite agents, HDAC inhibitors, proteosome inhibitors, immunotherapeutic agents, FLT-3 EGFR, MEK, PI3K and other protein kinase inhibitors, LSD1 inhibitors, and WNT pathway inhibitors, alkylating agents and DNA repair pathway inhibitors, anti-hormonal agents, anti-cancer antibodies, and other cytotoxic chemotherapy agents.

10. A method of alleviating, relieving or ameliorating a fibrotic disease in a mammal in need thereof comprising administering to said mammal an effective amount of the composition of claim 1.

11. The method of claim 10, wherein the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis.

* * * * *